(12) United States Patent
Clevelario et al.

(10) Patent No.: US 9,645,072 B2
(45) Date of Patent: May 9, 2017

(54) INTERMEDIATE SEALING FOR ULTRADEEP WATER APPLICATIONS

(71) Applicant: GE Oil & Gas UK Limited, Nailsea, Bristol (GB)

(72) Inventors: Judimar de Assis Clevelario, Rio de Janeiro (BR); Fabio de Souza Pires, Rio de Janeiro (BR); Felipe Areas Vargas, Niteroi (BR); Valdeir Tinoco da Silva, Rio de Janeiro (BR)

(73) Assignee: GE Oil & Gas UK Limited, Nailsea, Bristol (GB)

(*) Notice: Subject to any disclaimer, the term of this patent is extended or adjusted under 35 U.S.C. 154(b) by 92 days.

(21) Appl. No.: 14/409,955

(22) PCT Filed: Jun. 24, 2013

(86) PCT No.: PCT/EP2013/063103
§ 371 (c)(1),
(2) Date: Dec. 19, 2014

(87) PCT Pub. No.: WO2014/001236
PCT Pub. Date: Jan. 3, 2014

(65) Prior Publication Data
US 2015/0330890 A1    Nov. 19, 2015

(30) Foreign Application Priority Data

Jun. 26, 2012  (EP) .................................... 12173647

(51) Int. Cl.
*G01N 19/04* (2006.01)
*F16L 17/02* (2006.01)
(Continued)

(52) U.S. Cl.
CPC .............. *G01N 19/04* (2013.01); *F16L 17/02* (2013.01); *F16L 33/01* (2013.01); *F16L 33/16* (2013.01);
(Continued)

(58) Field of Classification Search
CPC .......... G01N 19/04; F16L 17/02; F16L 33/16; F16L 33/32; F16L 33/01; F16L 2201/30; G01M 3/2853
(Continued)

(56) References Cited

U.S. PATENT DOCUMENTS 3,546,923 A * 12/1970 Nicholas ............. G01M 3/2853
                                                     73/40
6,125,693 A * 10/2000 Dubois ................... G01M 3/04
                                                     73/46

(Continued)

FOREIGN PATENT DOCUMENTS

| CN | 101501470 A | 8/2009 |
|---|---|---|
| CN | 101553682 A | 10/2009 |
| WO | WO2010/092326 A1 | 8/2010 |

OTHER PUBLICATIONS

International Search Report and Written Opinion of the International Searching Authority, mailed Oct. 28, 2013, for corresponding International Application No. PCT/EP2013/063103, 9 pages.
(Continued)

*Primary Examiner* — Hezron E Williams
*Assistant Examiner* — Marrit Eyassu
(74) *Attorney, Agent, or Firm* — Klarquist Sparkman, LLP (57) ABSTRACT

A sealing arrangement and a method for testing the integrity of a sealing arrangement of a flexible pipe are disclosed. The method includes locating a first annular sealing element and a second annular sealing element in a joint between two
(Continued)

elements of a flexible pipe, with a region of the joint therebetween; and pressurizing the region between the first sealing element and the second sealing element through a port extending towards the region to a predetermined pressure of 0.2 MP or greater.

11 Claims, 4 Drawing Sheets

(51) Int. Cl.
   *F16L 33/16* (2006.01)
   *F16L 33/32* (2006.01)
   *F16L 33/01* (2006.01)
   *G01M 3/28* (2006.01)
(52) U.S. Cl.
   CPC ........... *F16L 33/32* (2013.01); *G01M 3/2853* (2013.01); *F16L 2201/30* (2013.01)
(58) Field of Classification Search
   USPC .................................................. 73/40–49.8
   See application file for complete search history.

(56) References Cited

U.S. PATENT DOCUMENTS

| 6,923,477 | B2* | 8/2005 | Buon ................... F16L 33/003 138/109 |
| 2008/0017390 | A1* | 1/2008 | Bowie ................... F16L 55/124 166/387 |
| 2010/0146768 | A1 | 6/2010 | Sheldrake |
| 2011/0214771 | A1 | 9/2011 | Graham |

OTHER PUBLICATIONS

International Preliminary Report on Patentability and Written Opinion of the International Searching Authority, mailed Jan. 8, 2015, for corresponding International Application No. PCT/EP2013/063103, 7 pages.
Office Action and Search Report from Patent Office of the People's Republic of China, for Chinese Patent Application No. 201380034458.2, including English Translation, dated Oct. 8, 2016, 17 pages.

* cited by examiner

PRIOR ART

INTERMEDIATE SEALING FOR ULTRADEEP WATER APPLICATIONS

CROSS REFERENCE TO RELATED APPLICATIONS

This is the U.S. National Stage of International Application No. PCT/EP2013/063103, filed Jun. 24, 2013, which in turn claims priority to and the benefit of European Patent Application No. EP12173647.4, filed Jun. 26, 2012.

The present invention relates to the intermediate sealing for ultra-deep water applications. In particular, but not exclusively, the present invention relates to fluid sealing systems provided in end fittings of flexible pipes, including the seal configuration and the testing thereof.

Traditionally flexible pipe is utilised to transport production fluids, such as oil and/or gas and/or water, from one location to another. Flexible pipe is particularly useful in connecting a sub-sea location (which may be deep underwater, say 1000 meters or more) to a sea level location. The pipe may have an internal diameter of typically up to around 0.6 meters. Flexible pipe is generally formed as an assembly of a flexible pipe body and one or more end fittings. The pipe body is typically formed as a combination of layered materials that form a pressure-containing conduit. The pipe structure allows large deflections without causing bending stresses that impair the pipe's functionality over its lifetime. The pipe body is generally built up as a combined structure including metallic and polymer layers.

Unbonded flexible pipe has been used for deep water (less than 3,300 feet (1,005.84 meters)) and ultra deep water (greater than 3,300 feet) developments. It is the increasing demand for oil which is causing exploration to occur at greater and greater depths where environmental factors are more extreme. For example in such deep and ultra-deep water environments ocean floor temperature increases the risk of production fluids cooling to a temperature that may lead to pipe blockage. Increased depths also increase the pressure associated with the environment in which the flexible pipe must operate. As a result the need for high levels of performance from the layers of the flexible pipe body and the connections of pipe body layers with end fittings is increased.

Figure 1:
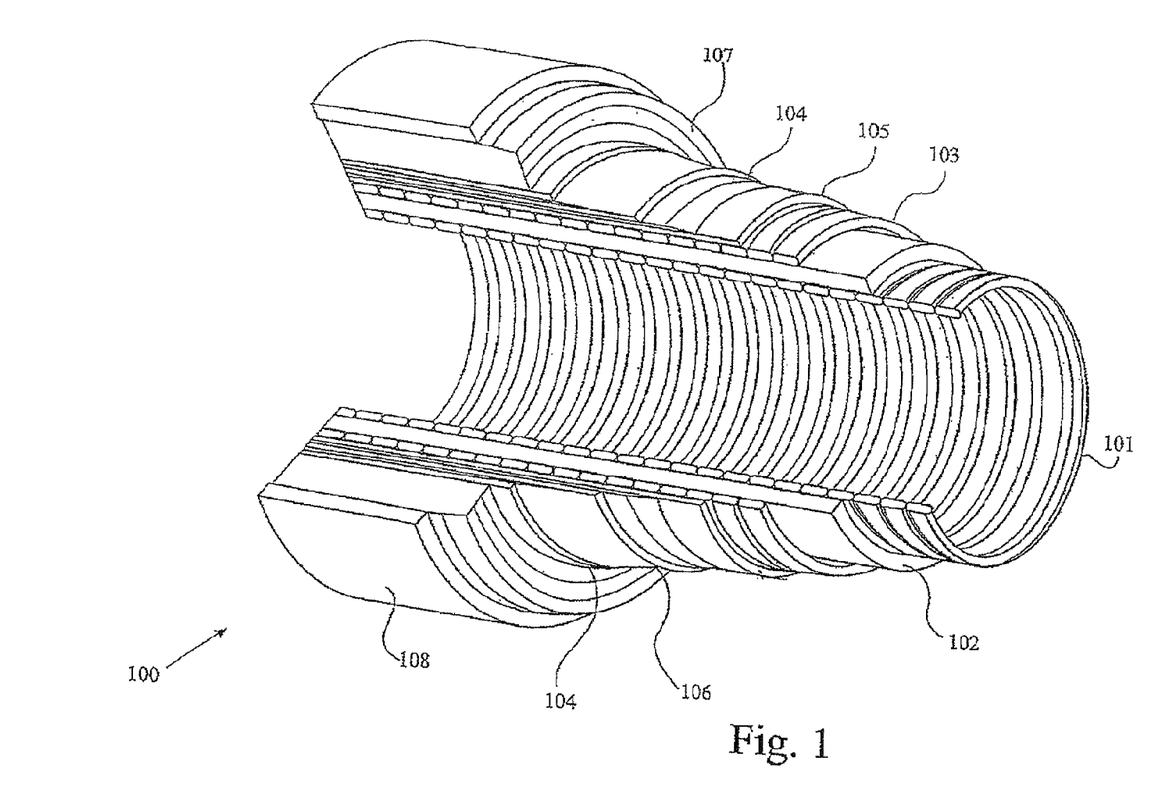
FIG. 1 illustrates a flexible pipe body.

A flexible pipe is an assembly of a portion of a pipe body and one or more end fittings in each of which a respective end of the pipe body is terminated. FIG. 1 illustrates how pipe body 100 may formed from a combination of layered materials that form a pressure-containing conduit. Although a number of particular layers are illustrated in FIG. 1, pipe body structures may include two or more coaxial layers manufactured from a variety of possible materials. For example, the pipe body may be formed from metallic layers, composite layers, or a combination of different materials. The layer thicknesses are shown for illustrative purposes only.

As illustrated in FIG. 1, a pipe body includes an optional innermost carcass layer 101. The carcass provides an interlocked construction that can be used as the innermost layer to prevent, totally or partially, collapse of an internal pressure sheath 102 due to pipe decompression, external pressure, and tensile armour pressure and mechanical crushing loads. The carcass layer is often a metallic layer, formed from stainless steel, for example. The carcass layer could also be formed from composite, polymer, or other material, or a combination of materials. Pipe body may be used without a carcass layer (i.e. smooth bore) or with a carcass (rough bore). The internal pressure sheath 102 acts as a fluid retaining layer and comprises a polymer layer that ensures internal fluid integrity. It is to be understood that this layer may itself comprise a number of sub-layers. It will be appreciated that when the optional carcass layer is utilised the internal pressure sheath is often referred to by those skilled in the art as a barrier layer. In operation without such a carcass (smooth bore operation) the internal pressure sheath may be referred to as a liner.

An optional pressure armour layer 103 is a structural layer that increases the resistance of the flexible pipe to internal and external pressure and mechanical crushing loads. The layer also structurally supports the internal pressure sheath, and typically may be formed as an interlocked construction of wires wound with a lay angle close to 90°. The pressure armour layer is often a metallic layer, formed from carbon steel, for example. The pressure armour layer could also be formed from composite, polymer, or other material, or a combination of materials.

The flexible pipe body also includes an optional first tensile armour layer 105 and optional second tensile armour layer 106. Each tensile armour layer is used to sustain tensile loads and internal pressure. The tensile armour layer is often formed from a plurality of metallic wires (to impart strength to the layer) that are located over an inner layer and are helically wound along the length of the pipe at a lay angle typically between about 10° to 55°. The tensile armour layers are often counter-wound in pairs. The tensile armour layers are often metallic layers, formed from carbon steel, for example. The tensile armour layers could also be formed from composite, polymer, or other material, or a combination of materials.

The flexible pipe body also typically includes optional layers of insulation 107 and an outer sheath 108, which comprises a polymer layer used to protect the pipe against penetration of seawater and other external environments, corrosion, abrasion and mechanical damage.

Each flexible pipe comprises at least one portion, sometimes referred to as a segment or section of pipe body 100 together with an end fitting located at at least one end of the flexible pipe. An end fitting provides a mechanical device which forms the transition between the flexible pipe body and a connector. The different pipe layers as shown, for example, in FIG. 1 are terminated in the end fitting in such a way as to transfer the load between the flexible pipe and the connector.

Figure 2:
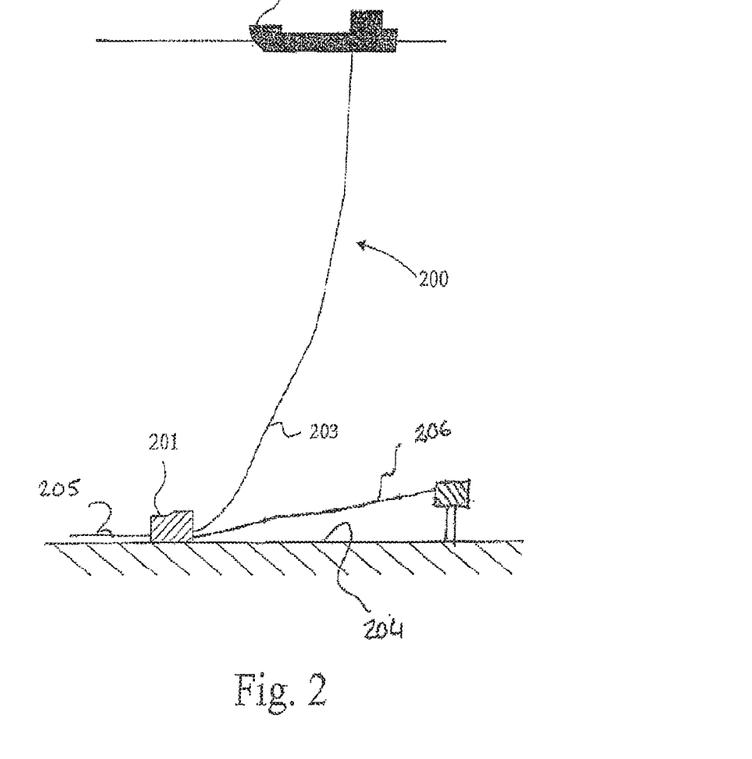
FIG. 2 illustrates a riser assembly.

The end fittings of a flexible pipe may be used for connecting segments of flexible pipe body together or for connecting them to terminal equipment such as a rigid sub-sea structures or floating facilities. As such, amongst other varied uses, flexible pipe can be used to provide a riser assembly for transporting fluids from a sub-sea flow line to a floating structure. In such a riser assembly a first segment of flexible pipe may be connected to one or more further segments of flexible pipe. Each segment of flexible pipe includes at least one end fitting. FIG. 2 illustrates a riser assembly 200 suitable for transporting production fluid such as oil and/or gas and/or water from a sub-sea location 201 to a floating facility 202.

Figure 3:
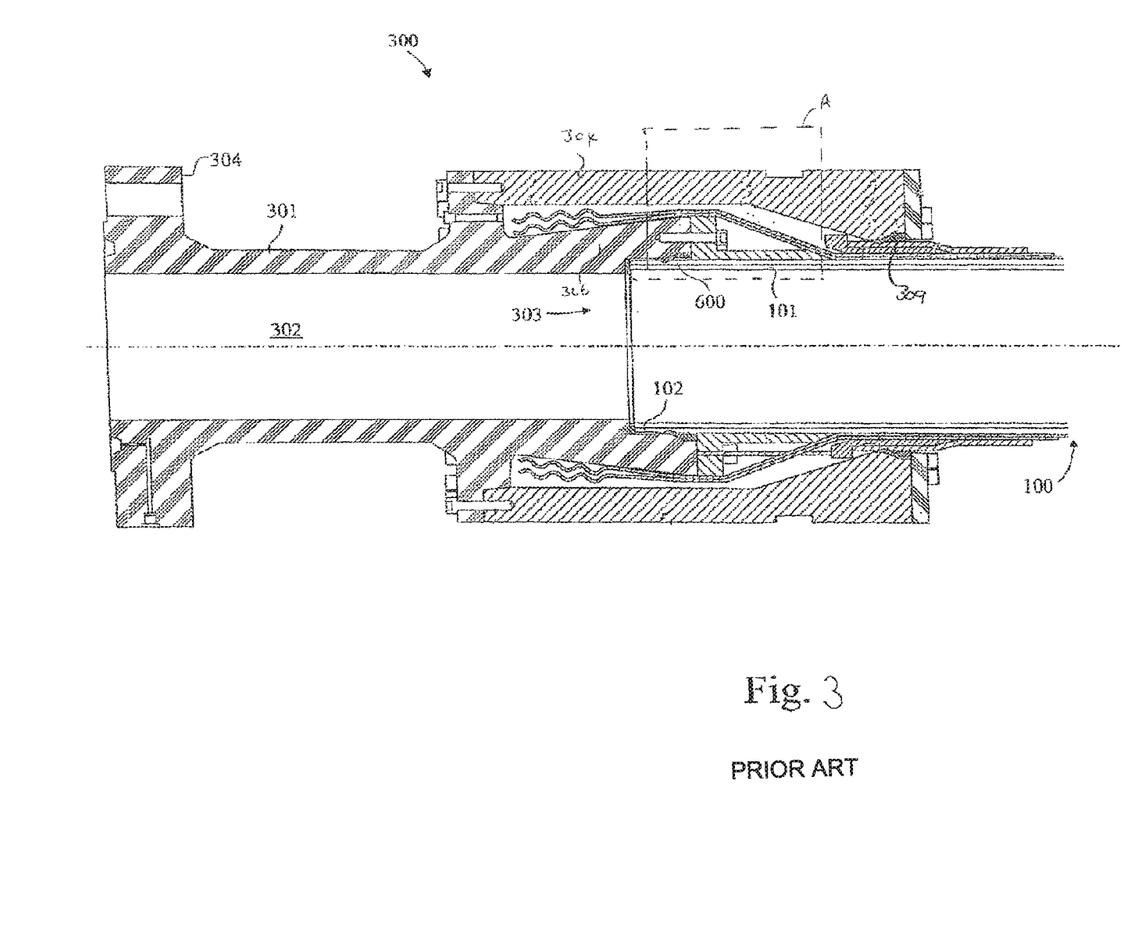
FIG. 3 illustrates an end fitting.

A cross-section of a known end fitting assembly 300, such as disclosed in WO2007/144552 or EP1867907, is shown in FIG. 3. The end fitting 300 includes an end fitting body 301, which includes an internal bore 302 running along its length. The end fitting body is made from steel or other such rigid material. At a first end of the end fitting body 301 there is defined an open mouth region 303 into which an end of a segment of flexible pipe body 100 is located and then terminated. At a further end of the end fitting body 301 is a connector 304. This is formed as a substantially disk-like flared region on the end fitting body. The connector can be connected directly to a matching connector of a further end fitting body of an adjacent segment of flexible pipe body. This can be done using bolts or some other form of securing mechanism. In such a configuration the end fittings would be located in a back-to-back configuration. Alternatively the connector 304 may be connected to a floating or stationary structure such as a ship, platform or other such structure. Various layers of flexible pipe body are introduced to the end fitting assembly, cut to appropriate length, and sealingly engaged with a particular portion of the end fitting.

There are varied problems associated with the provision of end fittings for ends of flexible pipe body. The end fittings must ensure both good fastening and good sealing. In particular, inner seal ring 600 and outer sealing ring 309 may be provided to seal between an adjacent layer of flexible pipe body and the end fitting. A seal is formed by a swaging action, which causes deformation of the sealing ring and/or adjacent layer of pipe body, and compression of the layer of pipe body, which may be of polymer, for example. End fittings vary in design so as to accommodate different variants of flexible pipe body. Certain end fitting designs may include a further sealing ring such as an intermediate sealing ring, which may be used to form a seal between an intermediate sheath layer of a flexible pipe body and the end fitting. Some known arrangements may have an increased risk of leaking as they cannot easily or reliably be tested during the assembly/fabrication stage of attaching the end fitting to the pipe body, so it cannot be known how effective such seals are.

To date, the testing of verification of sealing systems during assembly of the end fittings on the pipe body may be insufficient to prove integrity in service when the pipe is pressurised. This is because the materials used in the construction of the end fitting elements exhibit elastic material behaviour when subjected to loading, for instance when the pipe is pressurised. The amount of elastic movement/displacement of components will be determined from the pressure in the pipe and the material properties of the components. For example, sealed joints which rely on threaded fastener systems for their make-up forces and consequently their sealing integrity will require a high pre-loading of the fasteners during assembly to ensure that the compression force in the seal, required to maintain the seal integrity, are dominant even as the applied pressure in the pipe tries to separate the joint.

Figure 4:
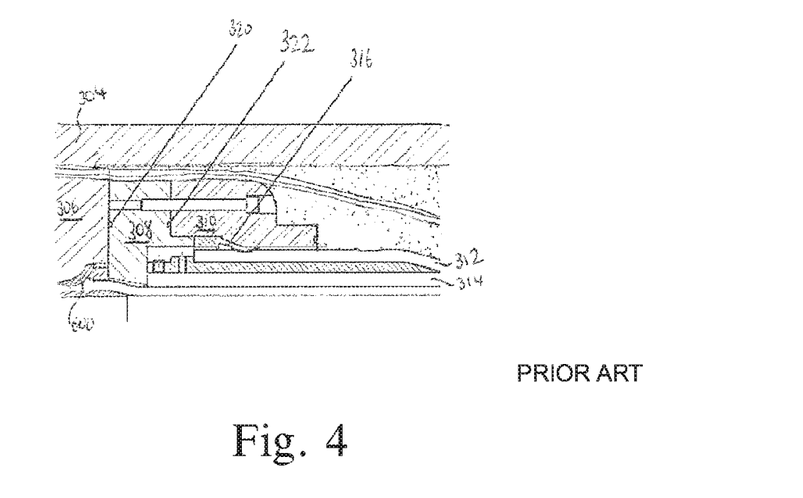
FIG. 4 illustrates a variation on the end fitting design.

FIG. 4 shows a variation on the arrangement shown in box A of FIG. 3. The arrangement shown includes an end fitting jacket 304, end fitting body 306, and inner sealing ring 600, as per FIG. 3. However, the assembly also includes a first collar member 308 and a second collar member 310 provided to terminate an intermediate sealing layer 312 of the pipe body. The intermediate sealing layer may be provided radially outwards of a pressure armour layer 314 and used to seal the pressure armour layer.

The assembly also includes an additional sealing ring 316 which is known as an intermediate sealing ring, because it seals against an intermediate sealing layer of the pipe body. In addition, the assembly includes O-rings 320, 322 to help block a potential leak pathway along the edges of the first collar member 308.

It will be known that O-rings are often used for efficient sealing, however the location and performance of O-ring seals is very dependent upon the properties and performance of the materials around them. The compression forces on either side of an O-ring seal arrangement are critical to the maintenance of a seal. The ability to prove the performance of a sealing system into service is difficult as it is not possible to perform a test on the known configurations as shown in FIG. 4 when the pipe is pressurised. Furthermore, if the collar member or other adjacent component of the end fitting assembly between which the O-ring is located were to loosen (i.e. move apart in an axial direction of the flexible pipe), e.g. because an axially extending bolt loosens, the O-ring may drop out of position in a radial direction of the pipe.

It has previously been impossible to test the integrity of the O-rings 320, 322 and sealing ring 316 in this arrangement. In addition there may be issues locating the O-rings correctly, and under high pressures when elastic flexing of some of the components takes place the compression force on these O-rings, required to maintain their seal integrity, may diminish or even be lost.

According to a first aspect of the present invention there is provided a method for testing the integrity of a sealing arrangement of a flexible pipe, comprising:
    locating a first annular sealing element and a second annular sealing element in a joint between two elements of a flexible pipe, with a region of the joint therebetween; and
    pressurising the region between the first sealing element and the second sealing element through a port extending towards the region to a predetermined pressure of about 0.2 MPa or greater.

According to a second aspect of the present invention there is provided an assembly for ensuring the integrity of a sealing arrangement of a flexible pipe, comprising:
    a first annular sealing element and a second annular sealing element in a joint between two elements of a flexible pipe, with a region of the joint therebetween; and
    a port extending towards the first sealing element for pressurising the region between the first sealing element and the second sealing element.

According to a third aspect of the present invention there is provided a method substantially as herein described with reference to the drawings.

According to a fourth aspect of the present invention there is provided an assembly substantially as herein described with reference to the drawings.

Certain embodiments of the invention provide the advantage that a sealing system is provided that has improved reliability to known arrangements. Certain embodiments of the invention provide a method of testing the sealing integrity of a sealing element in a flexible pipe prior to deployment. As such, the lifetime of the flexible pipe may be more accurately forecast.

Embodiments of the invention are further described hereinafter with reference to the accompanying drawings, in which.

In the drawings like reference numerals refer to like parts.

Figure 5:
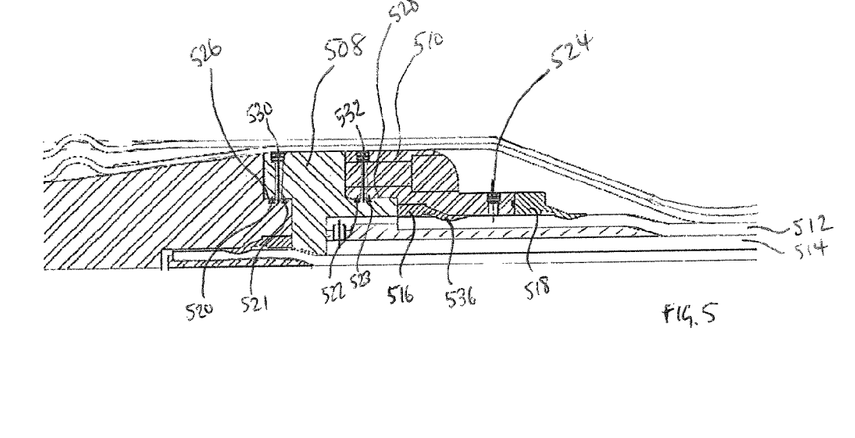
FIG. 5 illustrates a portion of an end fitting assembly.

FIG. 5 illustrates a cross-section of a portion of a sealing arrangement of an end fitting. The assembly includes a first collar member 508 and a second collar member 510 provided to terminate an intermediate sealing layer 512 of the pipe body. The intermediate sealing layer may be provided radially outwards of a pressure armour layer 514 and used to seal the pressure armour layer.

The assembly also includes intermediate sealing rings 516, 518 for blocking a potential leak pathway along the radially outer face of the intermediate sealing layer 512 and the first collar member 508. The first sealing ring is provided between the first collar member and the second collar member, and over a portion of the intermediate sealing layer 512. The second sealing ring is provided at an opposite side of the second collar member 510 and over a portion of the intermediate sealing layer 512. As such, in this example the first and second sealing rings have the same diameter (and radius). Between the sealing rings 516, 518 is a test port 524 provided in the second collar member 510, extending as a passageway from a radially outer surface of the second collar member to a radially inner surface of the collar member.

The first and second sealing rings are orientated in the same direction, which assists with their installation and energisation (their energisation is discussed in more detail below). That is, each sealing ring faces the same axial direction (with the wedge-like portion facing to the right in the cross-section of FIG. 5). This allows the two seals to be treated similarly when performing a swaging action on the seals to energise the seals. For example, a single axial motion in one direction may be used to energise both seals. In addition, the same orientation of both seals allows a simple installation technique to be used and provides a more reliable seal as stresses in the polymer barrier layer between the sealing rings during energisation are not acting against the sealing forces.

In addition, the assembly includes two pairs of O-rings 520, 521, 522, 523 to help block a potential leak pathway along the edges of the first collar member 508. The O-rings are coaxial and provided along surfaces 526, 528 of the first collar member 508 that extend around circumferential axes of the flexible pipe. In this example, the O-rings 520 and 521 have the same diameter, and the O-rings 522 and 523 have the same diameter. Between the O-rings 520, 521 is a test port 530 provided in the first collar member 508, extending as a passageway from a radially outer surface of the first collar member to a radially inner surface of the collar member. Between the O-rings 522, 523 is a test port 532 provided in the first collar member 508, extending as a passageway from a radially outer surface of the first collar member to a radially inner surface of the collar member.

To provide a good seal, a sealing ring should be energised by a swaging action. This involves the two adjacent elements, in the case of the sealing ring 516, the first collar member 508 and second collar member 510, being brought together (in either direction or simultaneously) until further movement is restricted. Then, the adjacent elements are brought closer together, which is likely to deform the wedge-like portion of the sealing ring 536 and urge the wedge-like portion into a close sealing configuration with the pipe layer below (intermediate sheath 512). The pipe layer may also deform somewhat.

Figure 6:
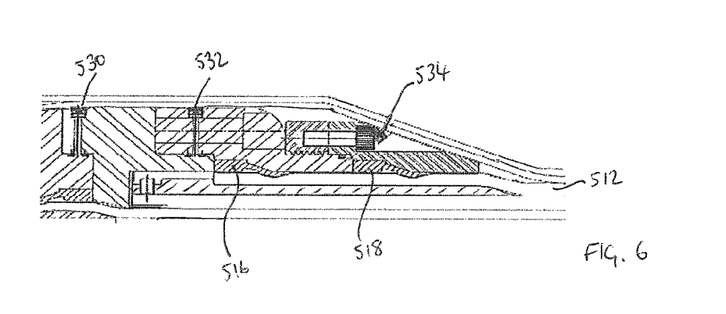
FIG. 6 illustrates the portion of FIG. 5 during assembly.

As shown in FIG. 6, to energise the sealing rings 516, 518, a swaging tool 534 is used, which is forced in a direction from right to left in the figure shown. Of course the collar members could alternatively be forced towards a stationary swaging tool, or all elements urged simultaneously together. This action energises both sealing rings as described above. The swaging tool may then be removed to provide access to the test port 524.

With the sealing rings in place and forming a seal, the test port 524 may be used to test the integrity of the sealing rings. In a testing mode, a fluid (e.g. water or air) may be introduced into the port 524 to pressurise the region between the two sealing rings. The pressure introduced may aptly be 2 MPa, or more. The pressure may be predetermined to simulate the hydrostatic pressure experienced under the sea in use. As such, the fluid may be introduced via port 524 and the fluid pressurised to a level that has been predetermined in accordance with the requirements of use of the pipe in service. Certain arrangements may warrant testing to 5 MPa, or 10 MPa, or 20 MPa, or 30 MPa, or 40 MPa or up to 50 MPa, for example.

With this arrangement, the joints between the sealing rings 516, 518 and the intermediate sealing layer 512 will receive pressurised fluid. Upon reaching a pressurized state, this region should not see a fall in pressure over the test period, due to the first and second sealing rings 516, 518. The region may be pressurised for a predetermined period, for example 5 minutes, or up to 2 hours or more. The period of testing will become less useful if pressure is held for many hours, as fluid may begin to permeate the polymer sheath 512. The pressure of the fluid under pressure is monitored over a test period. If the apparatus gives no indication of a leakage or failure, as signified by a drop in pressure, then the integrity of the seal 516 may be confirmed.

In addition to this test, a similar type of pressure test may be performed to test the pair of O-rings 520, 521 using the test port 530. Furthermore, a similar type of pressure test may be performed to test the pair of O-rings 522, 523 using the test port 532. This test on the O-rings effectively provides proof of integrity of those seals not only during the assembly process, but also when the pipe is pressurised, as their location and configuration ensures the performance of the seal is not diminished or lost as a result of the elastic behaviour of threaded fasteners holding a connection together, as would have been the case with previous designs.

Aptly, the O-ring pairs may be tested to a pressure of around 0.2 MPa.

Upon testing of the sealing ring 516 and O-rings 520, 521, 522, 523 with a positive result (i.e. the seals maintain their integrity under the applied pressure), the pressure may be removed, the ports closed, and the flexible pipe construction may be completed ready for use. The sealing ring 518 becomes effectively redundant, its only use being as part of the testing arrangement.

Figure 7:
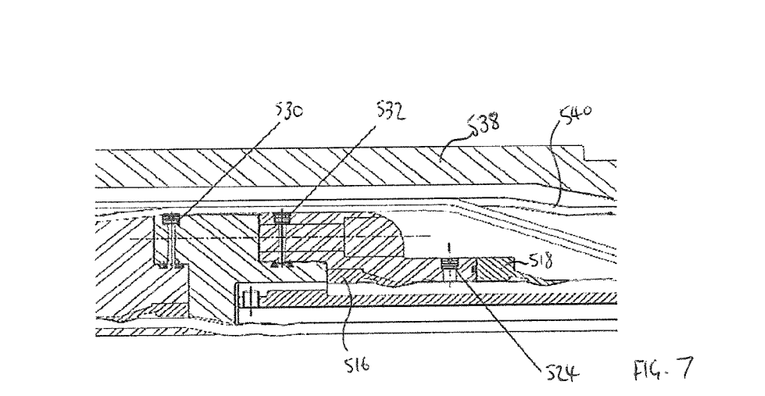
FIG. 7 illustrates the portion of FIG. 5 after further assembly.

FIG. 7 shows the arrangement after the additional parts of the end fitting have been applied, including an end fitting jacket 538 and a gas venting passageway 540. The remainder of the end fitting arrangement (not shown) may be provided in a known manner.

Various modifications to the detailed designs as described above are possible. For example, rather than a swaging tool, other arrangements may be used to energise the sealing rings. For example, a bolt may be used that is driven into the second collar member towards the first collar member and tightened to a degree that swages the sealing rings.

The sealing arrangement need not be designed to test an intermediate seal. A similar arrangement may be used to test a seal adjacent an outer collar member against an end fitting jacket, for example. Various layers and combinations of layers may be used, depending upon the required conditions of the flexible pipe.

With the above-described arrangement, it is possible to test the reliability of a sealing element to be used in a flexible pipe to be used at great depths under the sea, such as 1000 m or more and/or operating at high pressure. It is particularly useful to be able to have a high degree of confidence in the performance of a sealing element, because it is impossible to replace a faulty sealing element after deployment into the sea without completely re-terminating the pipe, which involves removing the pipe from its in-use location, removing the end fitting including the faulty sealing element, and re-fitting a new end fitting arrangement, before reuse of the pipe is possible.

By forming a chamber between a first and second sealing element, high pressure can be applied to test the integrity of at least one of the sealing elements required, yet without subjecting the remainder of the pipe to that high pressure. As such, the high pressure is applied only at the point of the pipe to be tested.

With the above-described invention, a sealing element may be tested during construction of a flexible pipe to ensure its sealing integrity prior to deployment of the flexible pipe.

For certain flexible pipe body arrangements, it is useful to provide a sealing layer (an intermediate seal) over the pressure armour layer. Then the pressure armour layer and a carcass layer may both be used to give pressure resistance to the pipe. With this invention, it can be assured that the pressure armour layer will not be flooded by hydrostatic pressure from the surrounding sea. As such, the performance of the pressure armour layers can be relied upon as part of the pressure (pipe collapse) resisting layers for ultradeep water applications.

It will be clear to a person skilled in the art that features described in relation to any of the embodiments described above can be applicable interchangeably between the different embodiments. The embodiments described above are examples to illustrate various features of the invention.

Throughout the description and claims of this specification, the words "comprise" and "contain" and variations of them mean "including but not limited to", and they are not intended to (and do not) exclude other moieties, additives, components, integers or steps. Throughout the description and claims of this specification, the singular encompasses the plural unless the context otherwise requires. In particular, where the indefinite article is used, the specification is to be understood as contemplating plurality as well as singularity, unless the context requires otherwise.

Features, integers, characteristics, compounds, chemical moieties or groups described in conjunction with a particular aspect, embodiment or example of the invention are to be understood to be applicable to any other aspect, embodiment or example described herein unless incompatible therewith. All of the features disclosed in this specification (including any accompanying claims, abstract and drawings), and/or all of the steps of any method or process so disclosed, may be combined in any combination, except combinations where at least some of such features and/or steps are mutually exclusive. The invention is not restricted to the details of any foregoing embodiments. The invention extends to any novel one, or any novel combination, of the features disclosed in this specification (including any accompanying claims, abstract and drawings), or to any novel one, or any novel combination, of the steps of any method or process so disclosed.

The reader's attention is directed to all papers and documents which are filed concurrently with or previous to this specification in connection with this application and which are open to public inspection with this specification, and the contents of all such papers and documents are incorporated herein by reference.

The invention claimed is:

1. A method for testing the integrity of a sealing arrangement of a flexible pipe, comprising:
    locating a first annular sealing element and a second annular sealing element in a joint between two elements of a flexible pipe, with a region of the joint therebetween; and
    pressurising the region between the first sealing element and the second sealing element through a port extending towards the region to a predetermined pressure of about 0.2 MPa or greater, and
    wherein the first and second sealing elements are sealing rings each having a cross-section comprising a wedge-like portion, and wherein the first and second sealing elements are oriented in the same axial direction such that the wedge-like portion of each sealing element faces an open mouth of an end fitting assembly into which an end of a flexible pipe body of the flexible pipe is located.

2. A method as claimed claim 1 wherein the first sealing element has a diameter equal to the second sealing element.

3. A method as claimed in claim 1 wherein the two elements of the flexible pipe are a first collar member and a second collar member.

4. A method as claimed in claim 1 wherein the first and second sealing elements are provided adjacent to and radially outwards of a polymer sealing layer of the flexible pipe body.

5. A method as claimed in claim 1 further comprising the step of energising the first and second sealing elements by urging one or both of the two elements of the flexible pipe towards the other element.

6. A method as claimed in claim 1 wherein the predetermined pressure is about 0.2 to 50 MPa.

7. A method as claimed in claim 1 further comprising
    locating a third annular sealing element and a fourth annular sealing element in a joint between two elements of a flexible pipe, with a region of the joint therebetween; and
    pressurising the region between the third sealing element and the fourth sealing element through a port extending towards the region to a predetermined pressure of 5 MPa or greater.

8. An assembly for ensuring the integrity of a sealing arrangement of a flexible pipe, comprising:
    a first annular sealing element and a second annular sealing element in a joint between two elements of a flexible pipe, with a region of the joint therebetween; and
    a port extending towards a region between the first sealing element and the second sealing element for pressurising the region between the first sealing element and the second sealing element,
    wherein the first and second sealing elements are sealing rings each having a cross-section comprising a wedge-like portion, and wherein the first and second sealing elements are oriented in the same axial direction such that the wedge-like portion of each sealing element faces an open mouth of an end fitting assembly into which an end of a flexible pipe body of the flexible pipe is located.

9. An assembly as claimed in claim 8 wherein the first and second sealing elements are swaged into position.

10. An assembly as claimed in claim 8 wherein the two elements of the flexible pipe are a first collar member and an end fitting body.

11. An assembly as claimed in claim 8 wherein the two elements of the flexible pipe are a first collar member and a second collar member.

\* \* \* \* \*